US00PP30185P2

(12) United States Plant Patent
Verhoef

(10) Patent No.: US PP30,185 P2
(45) Date of Patent: Feb. 12, 2019

(54) ***WEIGELA* PLANT NAMED 'SPRING2'**

(50) Latin Name: *Weigela florida*
Varietal Denomination: Spring2

(71) Applicant: Gijsbertus Verhoef, Hazerswoude-Dorp (NL)

(72) Inventor: Gijsbertus Verhoef, Hazerswoude-Dorp (NL)

( * ) Notice: Subject to any disclaimer, the term of this patent is extended or adjusted under 35 U.S.C. 154(b) by 0 days.

(21) Appl. No.: 15/732,355

(22) Filed: Oct. 30, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Weigela florida*, 'Spring2', characterized by its very compact plant habit, its glossy foliage that is black-purple in color, and its abundance of flowers in late spring.

2 Drawing Sheets

Botanical classification: *Weigela florida.*
Variety Denomination: 'Spring2'.

BACKGROUND OF THE INVENTION

The present invention relates to a new and distinct cultivar of *Weigela* and will be referred to hereafter by its cultivar name, 'Spring2'. 'Spring2' represents a new cultivar of *Weigela*, a deciduous shrub grown for landscape use.

The new cultivar originated as a seedling in a trial field that was planted with seeds collected from open pollination of *Weigela* 'Tango' (not patented) in Hazerswoude-Dorp, The Netherlands. The pollen parent is therefore unknown. 'Spring2' was selected as a single unique plant in July of 2007.

Asexual propagation of the new cultivar was first accomplished by softwood stem cuttings by the Inventor in June of 2008 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Spring2' as a unique cultivar of *Weigela.*

1. 'Spring2' exhibits a very compact plant habit.
2. 'Spring2' exhibits glossy foliage that is black-purple in color.
3. 'Spring2' exhibits an abundance of flowers in late spring.

The seed parent of 'Spring2', 'Tango', differs from 'Spring2' in having a less compact plant habit, in having foliage that is much lighter in color and in producing less flowers. 'Spring2' can also be compared to the *Weigela florida* cultivars 'Verweig3' (not patented) and 'Elvera' (U.S. Plant Pat. No. 12,217). Both 'Verweig3' and 'Elvera' are similar to 'Spring2' in having foliage that is dark-purple in color. 'Verweig3' differs from 'Spring2' in having significantly less flowers and a less compact plant habit. 'Elvera' differs from 'Spring2' in having significantly less flowers.

BRIEF DESCRIPTION OF THE DRAWINGS

The accompanying colored photographs were taken in August and illustrates the overall appearance and distinct characteristics of 28 month-old plants (pruned back to 10 cm above the soil level 3 months prior to photographing) of the new *Weigela* as grown outdoors in a field Hazerswoude-Dorp, The Netherlands.

The photograph in FIG. 1 provides an overall view of the growth habit of 'Spring2'.

Figure 1:
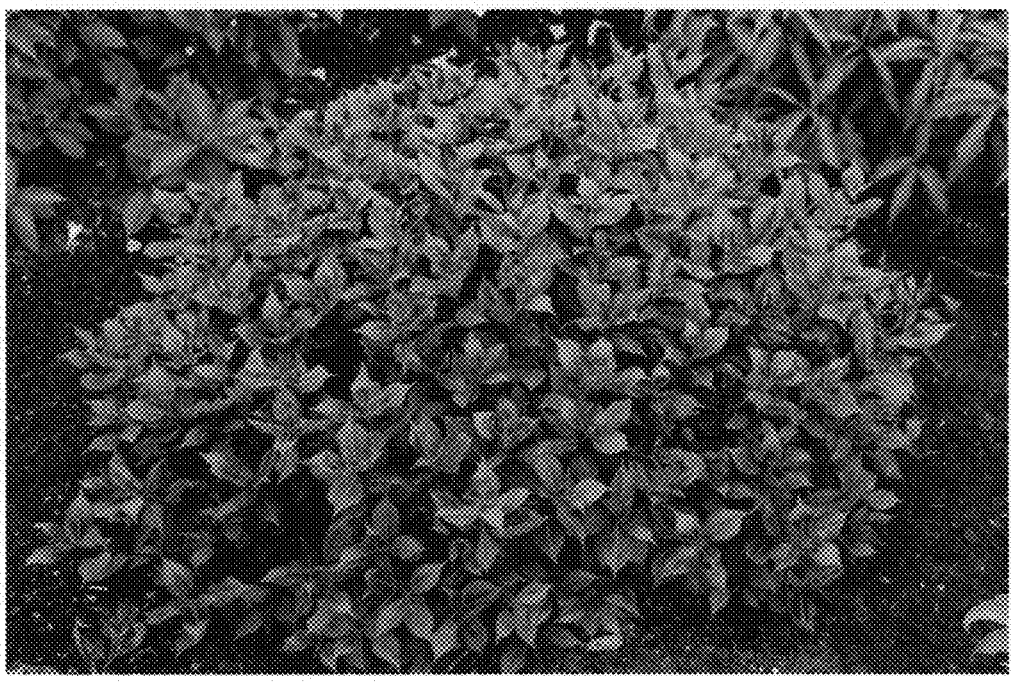
Figure 2:
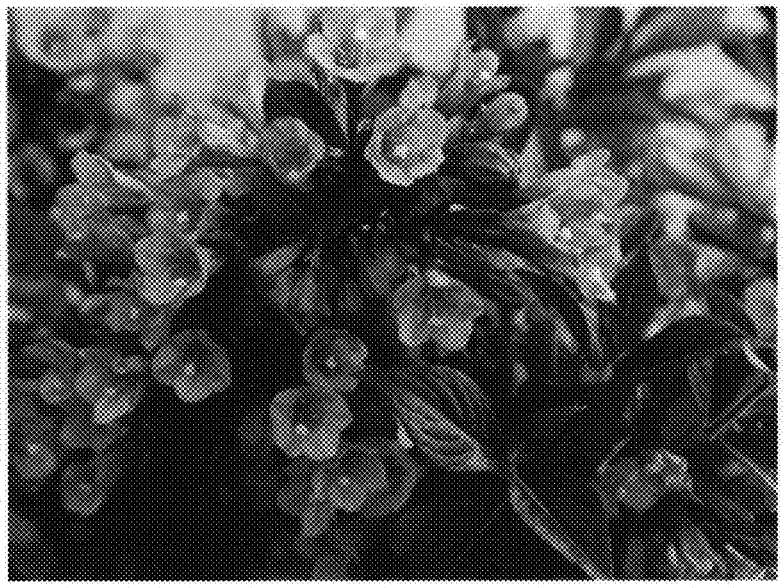

The photograph in FIG. 2 provides a close-up view of the flowers of 'Spring2'.

Figure 3:
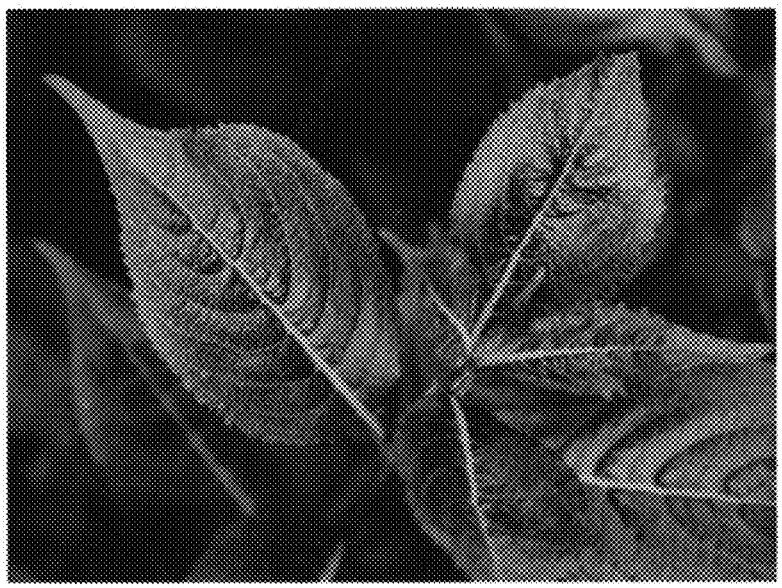

The photograph in FIG. 3 provides a close-up view of the foliage of 'Spring2'.

The colors in the photographs may differ slightly from the color values cited in the detailed botanical description, which accurately describe the colors of the new *Weigela.*

DETAILED BOTANICAL DESCRIPTION

The following is a detailed description of 28-month-old plants ((pruned back to 10 cm above the soil level 3 months prior to describing) of the new cultivar as grown outdoors in a field in Hazerswoude, The Netherlands. Hazerswoude-Dorp, Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period.*—Blooms heavily in late spring in The Netherlands.

*Plant type.*—Deciduous flowering shrub.

*Plant habit.*—Very compact, broadly spreading flattened mound, freely branched, nearly dwarf stature.

*Plant size*.—Reaches about 41 cm in height and 91 cm in width as a 28-month old plant and 70 cm in height and 125 cm in width as a mature plant in the landscape.

*Cold hardiness*.—At least in U.S.D.A. Zone 5.

*Diseases and pests*.—No susceptibility to resistance to diseases or pests has been observed.

*Root description*.—Fibrous, moderately dense.

*Propagation*.—Softwood stem cuttings.

*Root initiation*.—An average of 6 weeks.

*Root development*.—An average of 3 months to produce a young plant.

*Growth rate*.—Moderate.

Branch description:

*Branch shape*.—Rounded, young stems slightly angulate with four angles, two of which are slightly more pronounce.

*Branch color*.—New growth; 144A to 144B, mature wood; between 183A and N186C, bark; 199B to 199C.

*Branch size*.—An average of 27.1 cm in length and 3 mm in diameter.

*Branch surface*.—New growth; moderately glossy, with more pronounced angles densely covered with short adpressed strigose hairs an average of 0.5 mm in length and 157D in color.

*Stem aspect*.—Upright to outward at an average angle of 30°.

*Branching*.—An average of 128 main basal branches and 100 lateral branches.

Foliage description:

*Leaf shape*.—Ovate to obovate.

*Leaf division*.—Simple.

*Leaf base*.—Short attenuate to near obtuse.

*Leaf apex*.—Apiculate to aristate.

*Leaf fragrance*.—None.

*Leaf aspect*.—Held in an average angle of 45° to lateral branch.

*Leaf venation*.—Pinnate, color upper surface 146D, color lower surface N148B to N148C.

*Leaf margins*.—Finely serrate.

*Leaf arrangement*.—Opposite.

*Leaf attachment*.—Petiolate.

*Leaf surface*.—Both surfaces moderately rugose, upper surface; smooth, glabrous, glossy, main veins sparsely covered with very short hairs; an average of 0.2 mm in length and 157D in color, lower surface smooth, glabrous, moderately glossy, main and secondary veins moderately covered with very short hairs average of 0.3 mm in length and 157D in color.

*Leaf size*.—An average of 5.8 cm in length and 3.1 cm in width.

*Leaf quantity*.—An average of 26 per lateral branch.

*Leaf color*.—Newly expanded leaves; upper and lower surface 200A, mature leaves; upper surface a color between 200A and 203B, lower surface a color between N200A and N200B.

*Petioles*.—Average of 5 mm in length, 2 mm in width, flattened, upper surface color N148C to N148D, margined 177A to 177B, lower surface color 152D, both surfaces are slightly glossy and sparsely to moderately covered with very short pubescence 0.3 mm in length and 157D in color, strong.

*Stipules*.—None.

Inflorescence description:

*Inflorescence type*.—Solitary, in pairs, or in small clusters at terminus and leaf axils.

*Inflorescence size*.—7.2 cm in height, 5.1 cm in diameter.

*Flower buds*.—Oblanceolate in shape, an average of 2 cm in depth and 7 mm in diameter, N45C in color, matte surface, sparsely covered with very short hairs an average of 0.2 mm in length, too small to measure color.

*Flower fragrance*.—None.

*Lastingness of flowers*.—About 12 days, self-cleaning.

*Flower aspect*.—Outward to upright.

*Flower quantity*.—An average 11 per inflorescence, 200 buds and flowers per plant.

*Flower type*.—Tubular.

*Flower size*.—Average of 1.6 cm in height, 1.6 cm in diameter, 3 cm in depth, throat; 9 mm in diameter, tube; 2.2 cm in length, 1 cm in diameter.

*Peduncles*.—Average of 1.5 cm in length and 1.5 mm in diameter, held straight on top of lateral branch, moderate strength, slightly glossy surface, 144B in color, wings on peduncles sparsely covered with short hairs, 0.3 mm in length and too small to measure color.

*Calyx*.—Rotate in shape, an average of 6 mm in depth and 3 mm in width.

*Sepals*.—5, rotate, linear in shape, narrowly acute apex, cuneate base, entire margin, an average of 6 mm in length and 1 mm in width, color; when opening and fully open upper surface 145C and tinged 178B, when opening and fully open lower surface 145C.

*Petals*.—5, lower 62% fused into tube, spathulate in shape, margin entire on free portion, apex obtuse, an average of 2.7 cm in length, 9 mm in width, upper and lower surface glabrous and moderately velvety, color; when opening and fully open upper surface 53C, when opening lower surface N45B to N45C, when fully open lower surface 53B, throat color inner and outer surface 53C to 53D, tube color inner surface 53D to 54A, lower surface 53B.

Reproductive organs:

*Gynoecium*.—Pistil; 1, average of 3 cm in length, style; average of 2.8 cm in length, and 69D in color, fading towards the proximal end to 150D in color, stigma; club-shaped, 2 mm in length and diameter, 150D in color, ovary; 146B in color.

*Androcoecium*.—Stamens; 5, filaments; 69C to 69D in color and an average of 1 cm in length, anthers; 161C in color, an average of 4 mm in length and 0.5 mm in width, narrowly oblong in shape, pollen; low in quantity and 165C in color.

*Fruit and seed*.—No fruit or seed production has been observed to date.

It is claimed:

1. A new and distinct cultivar of *Weigela* plant named 'Spring2' as herein illustrated and described.

* * * * *